United States Patent [19]

Van Berkel et al.

[11] 4,298,757

[45] Nov. 3, 1981

[54] 2-[2-(2,2-DIHALOVINYL)-3,3-DIMETHYLCYCLOPROPYL]VINYL ALKANOATES

[75] Inventors: Johannes Van Berkel; Hendrik C. Kelderman, both of Amsterdam, Netherlands

[73] Assignee: Shell Oil Company, Houston, Tex.

[21] Appl. No.: 55,858

[22] Filed: Jul. 9, 1979

[30] Foreign Application Priority Data

Jul. 19, 1978 [GB] United Kingdom ............... 30337/78

[51] Int. Cl.$^3$ ..................... C07C 69/145; C07C 69/24
[52] U.S. Cl. .................................... 560/231; 260/339; 560/238; 562/506; 568/303; 568/347; 568/420; 568/591

[58] Field of Search .............................. 560/231, 238

[56] References Cited

FOREIGN PATENT DOCUMENTS 40-21057  5/1965  Japan ................................. 560/238

Primary Examiner—Vivian Garner

[57] ABSTRACT 2-(2,2-Dihalovinyl-3,3-dimethylcyclopropyl)vinyl alkanoates in which the alkanoate moiety contains from two to six carbon atoms are new chemical compounds useful as intermediates in the preparation of certain pyrethroid acids. The alkanoates are prepared by reacting 2-(2,2-dihalovinyl-3,3-dimethylcyclopropyl)ethanal with the appropriate alkanoic acid anhydride.

3 Claims, No Drawings

2-[2-(2,2-DIHALOVINYL)-3,3-DIMETHYLCYCLO-PROPYL]VINYL ALKANOATES

BACKGROUND OF THE INVENTION

1. Field of the Invention

The present invention is directed to new 2-[2-(2,2-dihalovinyl)-3,3-dimethylcyclopropyl]vinyl alkanoates, their preparation and their use as intermediates in the preparation of certain synthetic pyrethroids.

2. Summary of the Invention

The present invention is directed to 2-[2-(2,2-dihalovinyl)-3,3-dimethylcyclopropyl]vinyl alkanoates having the formula I

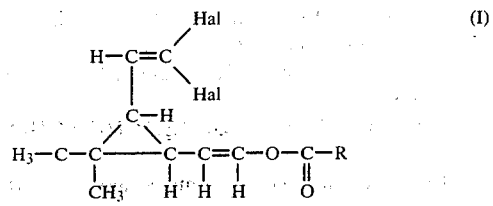

wherein each Hal independently is a chlorine, fluorine or bromine atom, R is an alkyl group containing from 1 to 5 carbon atoms. The acetate, wherein Hal is chlorine and R in the formula is methyl, is preferred. The alkanoates may be used as an intermediate in the preparation of pyrethroid esters of 2-(2,2-dihalovinyl)-3,3-dimethylcyclopropanecarboxylic acid. The alkanoates according to the invention have two asymmetric carbon atoms in the cyclopropane ring and, therefore may have the (1R,cis), (1R,trans), (1S,cis) or (1S,trans) configuration. The nomenclature used herein to describe the spatial configurations have been defined by M. Elliott et al. in Nature, 248 (1974), 710-711. Among the four spatial configurations of the said alkanoates the (1R,cis) configuration is preferred, because among these four spatial configurations of the pyrethroid esters of 2-(2,2-dihalovinyl)-3,3-dimethylcyclopropanecarboxylic acid the esters with the (1R,cis) configuration have the highest pesticidal activity.

The invention also provides a process for the preparation of 2-[2-(2,2-dihalovinyl)-3,3-dimethylcyclopropyl]-vinyl alkanoates wherein each halo independently is chloro, fluoro or bromo which comprises reacting 2-(2,2-dihalovinyl-3,3-dimethylcyclopropyl)ethanal with the appropriate anhydride of an alkanoic acid.

The process is suitably carried out in the presence of an amine, preferably a trialkylamine containing from 2-6 carbon atoms in each alkyl group. Starting from the (1R,cis) isomer of 2-(2,2-dimethylcyclopropyl)ethanal, the process of the invention affords 2-(2,2-dimethylcyclopropyl)vinyl alkanoates exclusively in the (1R,cis) configuration.

According to another aspect of the invention, 2-(2,2-dihalovinyl)-3,3-dimethylcyclopropanecarboxylic acid is prepared by ozonolysis of a 2-(2,2-dihalovinyl-3,3-dimethylcyclopropyl)vinyl alkanoate followed by oxidative decomposition of the peroxidic ozonolysis product obtained. Ozonolysis of organic compounds and oxidative decomposition of the peroxidic ozonlysis product obtained is described in, for example, Chemical Reviews 53 (1958), 925-995. The oxidative decomposition may be carried out in the presence of hydrogen peroxide or a per acid, and, if desired, in the presence of a base, for example an alkali metal hydroxide. The presence of a base will yield a salt of 2-(2,2-dihalovinyl)-3,3-dimethylcyclopropanecarboxylic acid; this salt can be converted into the free acid by acidification procedures well known in the art.

The 2-[2-(2,2-dihalovinyl)-3,3-dimethylcyclopropyl]ethanal starting material for the present process is prepared from 2-(2,2-dimethoxyethyl)-3,3-dimethylcyclopropanecarbaldehyde, which is prepared as described in U.S. patent application Ser. No. 965,951, filed Dec. 4, 1978, the pertinent disclosures of which are incorporated herein by references, or from 4-hydroxy-2-carene by ozonolysis followed by reduction of the resulting product, both in the presence of an alkanol, to yield 4-acetyl-2-alkoxy-7,7-dimethyl-3-oxabicyclo[4.1.0]heptanes. The 2-methoxy compound is the preferred pyrethroid intermediate and is hydrolyzed with aqueous acid to yield 2-(2-hydroxy-3-oxobutyl)-3,3-dimethylcyclopropanecarbaldehyde which is readily converted to 1-(2-formyl-3,3-dimethylcyclopropyl)-3-oxo-2-butyl acetate by treatment with, e.g., acetyl halide. This acetate is then added to the product of the reaction of a tri(dialkylamino)phosphine or an alkyl ester of an ortho phosphorous acid bis(dialkylamide) with a compound generating a dihalocarbene to yield 1-[2-(2,2-dihalovinyl)-3,3-dimethylcyclopropyl]-3-oxo-2-butyl acetate. Oxidation of this compound, e.g., with peroxy acid, yields 2-[2-(2,2-dihalovinyl)-3,3-dimethylcyclopropyl]ethylidene diacetate. These reactions are described in the concurrently filed U.S. patent application No. 55,854.

The ethylidene diacetate is readily hydrolyzed, e.g., in the presence of acid, to yield 2-[2-(2,2-dihalovinyl)-3,3-dimethylcyclopropyl]-ethanal as described in the concurrently filed U.S. patent application Ser. No. 55,855, U.S. Pat. No. 4,222,964.

ILLUSTRATIVE EMBODIMENTS

The following embodiments are provided to illustrate the present invention and should not be regarded as limiting the invention in any way. Yields and purities were determined by means of gas-liquid chromatography and nuclear magnetic resonance (NMR) spectroscopy. The NMR data quoted were recorded at 90 MHz using solutions of the compounds in deuterochloroform; the absorptions given are relative to a tetramethylsilane standard.

EMBODIMENT I (1R,cis)-2-[2-(2,2-dichlorovinyl)-3,3-dimethylcyclopropyl]ethanal dimethyl acetal Tri(dimethylamino)phosphine (168.3 mmol) was added over a period of 12 minutes to a stirred solution of carbon tetrachloride (167.4 mmol) in pentane (360 ml) kept at 0° C. under nitrogen in a 1-liter flask. Then, the mixture in the flask was stirred for 30 minutes at 0° C. This finished the first step.

At 0° C. (1R,cis)-2-(2,2-dimethoxyethyl)-3,3-dimethylcyclopropanecarbaldehyde (66.4 mmol) was added dropwise to the suspension in the flask over a period of nine minutes. The temperature was increased to 12° C. over a period of 15 minutes and stirring was continued at the temperature for a further 15 minutes. This finished the second step. Then water (75 ml) was added at 12° C. and—after removal of the aqueous phase—the organic phase was washed with two 35-ml portions of water. The washed organic phase was dried over anhydrous magnesium sulphate and the solvent was evaporated from the dried solution to give a residue (17.4 g) containing the desired product (100% (1R,cis), purity 88%, yield 91.1%).

The NMR spectrum of the desired product showed the following absorptions:

δ=1.00 ppm singlet H$_3$C—C—C$\underline{H}_3$

δ=3.33 ppm singlet C—(O—C$\underline{H}_3$)$_2$
δ=5.59 ppm doublet C=C$\underline{H}$
δ=1.13 ppm singlet $\underline{H}_3$C—C—CH$_3$
δ=4.33 ppm triplet (H$_3$C—O)$_2$—C$\underline{H}$—
multiplets for the two H atoms bound to the ring and for HC—C$\underline{H}_2$—CH.

EMBODIMENT II (1R,cis)-2-[2-(2,2-dichlorovinyl)-3,3-dimethylcyclopropyl]ethanal A 250-ml flask was charged with the residue (17.4 g, containing 60.5 mmol of (1R,cis)-2-[2-(2,2-dichlorovinyl)-3,3-dimethylcyclopropyl]ethanal dimethyl acetal obtained as described in Embodiment I above) and a 2/1 (v/v) mixture (90 ml) of acetic acid and water to which concentrated aqueous hydrochloric acid (0.02 ml. sp.gr. 1.19) had been added. The mixture in the flask was heated with stirring under nitrogen for two hours at 60° C. Then, most of the acetic acid and water was distilled off from the reaction mixture (60° C./13.3 kPa), the residue obtained was taken up in diethyl ether (100 ml), water (25 ml) was added to the etheral solution and the pH of the liquid was increased to 7 by addition of sodium hydrogen carbonate. The neutralized liquid was washed with 20-ml portions of water, the washed liquid was dried over anhydrous magnesium sulphate and the diethyl ether was distilled off from the dried liquid to give a residue (13.8 g) containing the desired product (100% (1R,cis), purity 82.1%, yield 90.4%). The NMR spectrum of this product showed the following absorptions:

δ=1.02 ppm singlet H$_3$C—C—C$\underline{H}_3$
δ=2.43 ppm double doublet $\underline{H}_2$C—C(O)H
δ=9.81 ppm triplet —C(O)$\underline{H}$
δ=1.21 ppm singlet $\underline{H}_3$C—C—CH$_3$
δ=5.57 ppm doublet Cl$_2$C=C$\underline{H}$
multiplets for the two H atoms bound to the ring.

EMBODIMENT III (1R,cis)-2-[2-(2,2-dichlorovinyl)-3,3-dimethylcyclopropyl]vinyl acetate A 250 ml flask was charged with 2-[2-(2,2-dichlorovinyl)-3,3-dimethylcyclopropyl]ethanal (13.7 g containing 54.3 mmol of the (1R,cis) form) obtained as in Embodiment II above and acetic anhydride (1450 mmol) to which triethylamine (157.7 mmol) had been added. The mixture in the flask was heated with stirring under nitrogen for 16 hours at 20° C. Then, acetic acid, acetic anhydride and triethylamine were distilled off from the reaction mixture at sub-atmospheric pressure, the residue obtained was taken up in diethyl ether (100 ml) to which water (50 ml) had been added and the pH of the liquid was increased to 7 by addition of sodium hydrogen carbonate. The neutralized liquid was washed with two 25-ml portions of water, the washed liquid was dried over anhydrous magnesium sulphate and the diethyl ether was distilled off from the dried liquid to give a residue (13.54 g) containing 2-[2-(2,2-dichlorovinyl]-3,3-dimethylcyclopropyl]vinyl acetate (100% (1R,cis), purity 97%, yield 97%). The cis/trans ratio (with respect to the HC=CH double bond) was 3/1 or 1/3.

The NMR spectrum of the desired product showed the following absorptions:

δ=1.07 ppm singlet H$_3$C—C—CH$_3$
δ=1.20 ppm singlet $\underline{H}_3$C—C—CH$_3$, HC=CHO trans or cis
δ=1.23 ppm singlet $\underline{H}_3$C—C—CH$_3$, HC=CHO cis or trans
δ=2.11 ppm singlet H$_3$C—C(O)O, HC=CHO trans or cis
δ=2.19 ppm singlet $\underline{H}_3$C—C(O)O, HC=CHO cis or trans
δ=4.63 ppm double doublet $\underline{H}$C=CHO, HC=CHO cis or trans
δ=5.18 ppm double doublet, $\underline{H}$C=CHO trans or cis
δ=5.65 ppm doublet Cl$_2$C=C$\underline{H}$
δ=7.21 ppm doublet, HC=C$\underline{H}$O, HC=CHO cis or trans
δ=7.23 ppm doublet HC=C$\underline{H}$O, HC=CHO trans or cis multiplets for the two H atoms bound to the ring.

EMBODIMENT IV (1R,cis)-2-(2,2-dichlorovinyl)-3,3-dimethylcyclopropanecarboxylic acid A mixture of oxygen and ozone (20 l/h, with 30 mmol of ozone per hour) was passed for 30 minutes at 0° C. through a solution of the residue (3.73 g, containing 14.53 mmol of (1R,cis) compound obtained as described in Embodiment III above), in ethyl acetate (20 ml). The mixture thus obtained was added at 0° C. to a solution of sodium hydroxide (37.5 mmol) in a mixture of water (5.0 ml) and 30% aqueous hydrogen peroxide (4.5 ml, containing 39.7 mmol of H$_2$O$_2$). The temperature of the mixture was allowed to increase to 20° C. and kept at this temperature for 6 hours, whilst nitrogen was passed through to effect the removal of ethyl acetate. Then, water (30 ml) and n-pentane (20 ml) were added to the mixture, the resulting two-phase system was allowed to separate by settling into a water layer and an organic layer and the organic layer was isolated and washed with a 5% aqueous solution (15 ml) of sodium hydroxide. The combined water layer and aqueous washing liquid were acidified with aqueous hydrochloric acid (sp. gr. 1.19) until a pH of 2.5, saturated with sodium chloride and extracted with four 25-ml portions of diethyl ether. The combined etheral extract phases were dried over anhydrous magnesium sulphate and the diethyl ether was distilled off from the dried liquid to give a residue (1.30 g) containing 2-(2,2-dichlorovinyl)-3,3-dimethylcyclopropanecarboxylic acid (100% (1R,cis), purity more than 98%, yield 42%). The optical rotation of this desired product measured in chloroform solution (2.3 g/100 ml chloroform) was [ε]$_D^{20}$+29.5°.

We claim:

1. A (1R,cis)-2-[2-(2,2-dihalovinyl)-3,3-dimethylcyclopropyl]vinyl alkanoate wherein each halo independently is chloro, fluoro or bromo and the alkanoate moiety contains from 2 to 6 carbon atoms.

2. An alkanoate according to claim 1 wherein each halo is chloro.

3. An alkanoate according to claim 2 which is the acetate.

* * * * *